US009655973B2

(12) United States Patent
Mann

(10) Patent No.: US 9,655,973 B2
(45) Date of Patent: May 23, 2017

(54) ORALLY ACTIVE, CELL-PENETRATING HOMING PEPTIDE AND METHODS OF USING SAME

(71) Applicant: Vascular Biosciences, San Diego, CA (US)

(72) Inventor: David M. Mann, San Diego, CA (US)

(73) Assignee: Vascular Biosciences, San Diego, CA (US)

( * ) Notice: Subject to any disclaimer, the term of this patent is extended or adjusted under 35 U.S.C. 154(b) by 0 days.

(21) Appl. No.: 14/383,818

(22) PCT Filed: Mar. 11, 2013

(86) PCT No.: PCT/US2013/030272

§ 371 (c)(1),
(2) Date: Sep. 8, 2014

(87) PCT Pub. No.: WO2013/134781

PCT Pub. Date: Sep. 12, 2013

(65) Prior Publication Data

US 2015/0133458 A1 May 14, 2015

Related U.S. Application Data

(60) Provisional application No. 61/609,224, filed on Mar. 9, 2012.

(51) Int. Cl.

| | |
|---|---|
| ***A61K 38/08*** | (2006.01) |
| ***A61K 47/42*** | (2017.01) |
| ***A61K 45/06*** | (2006.01) |
| ***C07K 7/06*** | (2006.01) |
| ***A61K 47/48*** | (2006.01) |
| ***A61K 9/00*** | (2006.01) |
| ***A61K 31/506*** | (2006.01) |
| ***A61K 31/519*** | (2006.01) |
| *A61K 38/00* | (2006.01) |

(52) U.S. Cl.

CPC ............ *A61K 47/42* (2013.01); *A61K 9/0053* (2013.01); *A61K 31/506* (2013.01); *A61K 31/519* (2013.01); *A61K 45/06* (2013.01); *A61K 47/48238* (2013.01); *C07K 7/06* (2013.01); *A61K 38/00* (2013.01)

(58) Field of Classification Search

CPC ...................................................... A61K 38/08
USPC ........................................................ 514/21.6
See application file for complete search history.

(56) References Cited

U.S. PATENT DOCUMENTS

| | | | | |
|---|---|---|---|---|
| 2010/0310531 A1 | 12/2010 | Wagner et al. | | |
| 2012/0034164 A1 | 2/2012 | Ruoslahti et al. | | |
| 2013/0098357 A1* | 4/2013 | Singh | A61K 45/06 | 128/200.23 |

OTHER PUBLICATIONS

Urakami et al. "Peptide-Directed Highly Selective Targeting of Pulmonary Arterial Hypertension." The American Journal of Pathology, (May 6, 2011) 178:2489-2495.

* cited by examiner

*Primary Examiner* — David Lukton

(74) *Attorney, Agent, or Firm* — Lewis Kohn & Walker LLP; David M. Kohn; Kari Moyer-Henry

(57) ABSTRACT

Disclosed are compositions and methods useful for oral delivery of targeted therapies for pulmonary diseases, fibrotic disorders and cancer. The compositions and methods are based on peptide sequences that selectively bind to and home to diseased tissue and enable targeted therapies to affect a beneficial therapeutic result. The disclosed targeting is useful for oral delivery of therapeutic and detectable agents to diseased tissue in an animal.

5 Claims, 18 Drawing Sheets

Oral CAR Exp Protocol

- SuHx 5w
- Injection after 3H from oral CAR
- Imatinib 5, 20mg/kg iv
- Control (saline) N=3 , Oral CAR 20mg/kg N=5

A.

B.

A.

B.

A.

B.

A.

B.

A.

B.

A.

B.

ORALLY ACTIVE, CELL-PENETRATING HOMING PEPTIDE AND METHODS OF USING SAME

RELATED APPLICATIONS

This application is a United States National Stage application claiming priority under 35 U.S.C. 371 from International Patent Application No. PCT/US13/30272 filed on Mar. 11, 2013, which claims priority from U.S. Provisional Application No. 61/609,224, filed on Mar. 9, 2012, the contents of which are hereby incorporated by reference herein.

GOVERNMENT SUPPORT STATEMENT

This invention was made with government support under grant 5R21H1106101 from the National Heart Lung Blood Institute of the NIH. The government has certain rights in the invention.

FIELD OF THE INVENTION

The present invention relates generally to the field of targeted therapies utilizing orally active peptides.

BACKGROUND OF THE INVENTION

Tissue regeneration, inflammation and tumors induce the growth of new blood vessels from pre-existing ones. This process, angiogenesis, is a vital requirement for wound healing as the formation of new blood vessels allows a variety of mediators, nutrients, and oxygen to reach the healing tissue (Martin 1997, Singer & Clark 1999, Falanga 2006, Folkman 2006). Newly formed blood vessels differ in structure from pre-existing vasculature. Such differences have been extensively characterized by comparing tumor vasculature to normal vessels (Ruoslahti, 2002). Angiogenic vessels in non-malignant tissues and in pre-malignant lesions share markers with tumor vessels (Gerlag et al, 2001), but distinct markers also exist (Hoffinan et al., 2003; Joyce et al., 2003).

Regarding tissue injuries, substantive basic science and clinical research have been conducted to evaluate the mechanisms of wound healing, the efficacy of various modalities for treatment of wounds, and the best methods for diagnosing wound infection. Tissue injuries caused by trauma, medical procedures, and inflammation are a major medical problem. Systemic medication is available for most major medical conditions, but therapeutic options in promoting tissue regeneration are largely limited to local intervention. As deep injuries and multiple sites of injury often limit the usefulness of local treatment, systemic approaches to tissue regeneration are valuable.

A major problem limiting tissue regeneration is scar formation. The response to tissue injury in adult mammals seems to be mainly focused on quick sealing on the injury. Fibroblast (astrocyte, smooth muscle cell) proliferation and enhanced extracellular matrix production are the main element of the scar formation, and the scar prevents tissue regeneration. In contrast, fetal tissues heal by a process that restores the original tissue architecture with no scarring. Transforming growth factor.beta. (TGF-.beta.) is a major factor responsible for impaired tissue regeneration, scar formation and fibrosis (Werner and Grose 2002; Brunner and Blakytny 2004; Leask and Abraham 2004).

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life. For decades, researchers have examined avenues to increase targeted specificity of therapeutics against only the disease, thereby preserving normal cellular integrity.

One manner by which therapeutic specificity may be increased is by targeting diseases at the cellular level. More specifically, therapeutics may be enhanced by interacting directly with those components at the level of the cell surface or membrane. These components include, among others, laminin, collagen, fibronectin and other proteoglycans. Proteoglycans are proteins classified by a posttranslational attachment of polysaccharide glycosaminoglycan (GAG) moieties each comprised of repeating disaccharide units. One monosaccharide of the disaccharide repeat is an amino sugar with D-glucosamine or galactosamine, and the other unit is typically, but not always, an uronic acid residue of either D-glucuronic acid or iduronic acid. Both units are variably N- and O-sulfated, which adds to the heterogeneity of these complex macromolecules. They can be found associated with both the extracellular matrix and plasma membranes. The most common GAG structures are dermatan sulfate (DS), chondroitin sulfate (CS), heparan sulfate (HS), keratan sulfate (KS), hyaluronic acid (HA), and heparin; representative structures for each disaccharide are shown below.

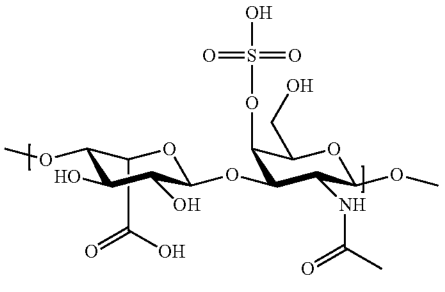

Dermatan sulfate

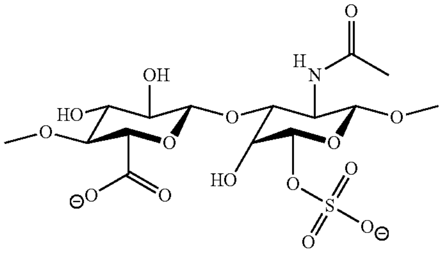

Chondroitin sulfate

-continued

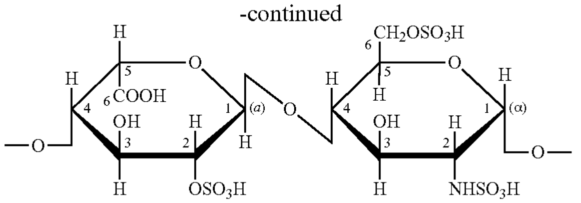

Heparan sulfate

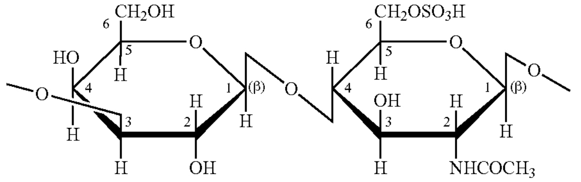

Keratan sulfate

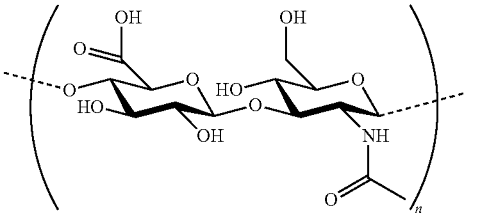

Hyaluronic acid

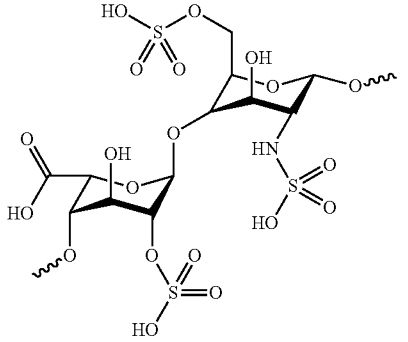

Heparin

These unbranched sulfated GAGs are defined by the repeating disaccharide units that comprise their chains, by their specific sites of sulfation, and by their susceptibility to bacterial enzymes known to cleave distinct GAG linkages. All have various degrees of sulfation which result in a high density of negative charge. Proteoglycans can be modified by more than one type of GAG and have a diversity of functions, including roles in cellular adhesion, differentiation, and growth. In addition, cell surface proteoglycans are known to act as cellular receptors for some bacteria and several animal viruses, including; foot-and-mouth disease type O virus, HSV types 1 and 2 and dengue virus. Accordingly, it would be advantageous from a therapeutic perspective to design agents which may be used at the cell surface level.

A major function of cell surface proteoglycans is in cell adhesion and migration, dynamic processes that are mediated through interactions between the proteoglycan GAG chains and extracellular matrix (ECM) components, such as laminin, collagen, and fibronectin. Proteoglycans also occur as integral components of basement membranes in most mammalian tissues. Interactions of these macromolecules with other ECM constituents contribute to the general architecture and permeability properties of the basement membrane, and thus these GAGs play a structural role. Proteoglycans and GAGs play a critical role in the pathophysiology of basement membrane-related diseases, including diabetes, atherosclerosis, and metastasis. In addition, cell-specific growth factors and enzymes are immobilized in the ECM and at the cell surface are bound to GAGs. As such, GAGs localize proteins and enzymes at their site of action to facilitate their physiological functions and in some cases prevent their proteolytic degradation. Proteoglycans and GAGs have been shown to regulate protein secretion and gene expression in certain tissues by mechanisms involving both membrane and nuclear events, including the binding of GAGs to transcription factors (Jackson, R. L. 1991). Limited information is available on the factors that regulate the expression of proteoglycans and their associated GAGs. There is a need in the art to develop cell-penetrating agents which bind to cell surface proteoglycans in order to have disease-specific efficacy.

US Patent Application Publication No. 20090036349 discloses a novel composition that selectively binds to regenerating tissue, wound sites and tumors in animals. In vivo screening of phage-displayed peptide libraries was used to probe vascular specialization. This screening method resulted in the identification of several peptides that selectively target phage to skin and tendon wounds. One peptide in particular was identified and contains the following sequence: CARSKNKDC (CAR) (SEQ ID NO:1). CAR displays homology to heparin-binding sites in various proteins, and binds to cell surface heparan sulfate and heparin. More specifically, CAR binds to glycosaminoglycan moieties in cell surface heparan sulfate proteoglycans (HSPGs) (Jarvinen and Ruoslahti 2007), and other cell-penetrating peptides have also mediated their entry into cells through binding to HSPGs (Poon and Gariépy 2007). HSPGs fine-tune mammalian physiology and orchestrate metabolism, transport, information transfer, support and regulation at the systemic level, as well as the cellular level (Bishop, Schuksz and Esko 2007). Overexpression of HSPG biosynthetic enzymes result in distinct heparan sulfate sulfation patterns (Pikas, Erikson and Kjellen 2000). The overexpression of HSPG biosynthetic enzymes have not been previously detected in a disease in which the co-administration of a cell penetrating peptide along with a bioactive agent which results in the disease-selective action of the co-administration of the peptide/agent combination.

Pulmonary arterial hypertension (PAH) is a progressive disorder characterized by abnormally high blood pressure in the pulmonary artery. The pulmonary artery carries blood from the heart to the lungs and the hypertension is derived from the high blood pressure within the artery. Hypertension occurs when most of the very small arteries throughout the lungs narrow in diameter, which increases the resistance to blood flow through the lungs. To overcome the increased resistance, pressure increases in the pulmonary artery and, in turn, within the right ventricle of the heart chamber that pumps blood into the pulmonary artery.

Signs and symptoms of PAH occur when increased pressure cannot fully overcome the elevated resistance and blood flow to the body is insufficient. Shortness of breath during exertion and fainting spells are the most common symptoms of PAH. People with this disorder may experience additional symptoms, particularly as the condition worsens. Other symptoms include dizziness, swelling (edema) of the ankles or legs, chest pain, and a racing pulse.

There is no known cure for pulmonary hypertension. The goal of treatment is to control symptoms and prevent more lung damage. It is important to treat medical disorders that cause pulmonary hypertension, such as obstructive sleep apnea, lung conditions, and heart valve disorders.

Many new treatment options for pulmonary hypertension and other forms of PAH are becoming available. Medicines currently used to treat pulmonary hypertension symptoms include calcium channel blockers and diuretics, as well as a host of pharmaceutical options, including eicosanoids and sildenafil citrate.

A major limitation in the treatment of PAH is the lack of pulmonary vascular selectivity. Recent studies have identified the cell-penetrating homing peptide, CAR, which specifically recognizes the neovasculature of wound tissue and homes to hypertensive pulmonary arteries, as being useful for a possible therapeutic candidate. Some cell-penetrating homing peptides have a unique ability to facilitate transportation of co-administered substances into the targeted cells/tissues. This is known as the "bystander effect" and has been considered very effective from a therapeutic perspective.

A need exists for a novel, orally active, cell-penetrating peptide in order to achieve a greater therapeutic efficacy in the treatment of PAH, and various other diseases. However, the oral delivery of therapeutic peptides and proteins has always been a significant challenge for the pharmaceutical industry. Several barriers encountered with the oral route are responsible for comparatively poor plasma levels of orally administered peptide drugs. The most important obstacles are the enzymatic barrier caused by luminally secreted and membrane-bound proteolytic enzymes and the absorption barrier, which consists of the mucus layer covering gastrointestinal (GI) mucosa, the mucosa per se and transmembrane-located efflux pumps such as P-glycoprotein (Martin, "Innovations in Oral Peptide Delivery", *Touchstone Health Sciences*, (2006)).

For years, injections remained the most common means for administering therapeutic proteins and peptides due to their otherwise poor oral bioavailability (Shaji J., "Protein and Peptide Drug Delivery: Oral Approaches", *Indian J Pharm Sci*., May-June; 70(3): 269-277 (2008)). However, the oral route would be preferred to any other route because of its high levels of patient acceptance and long term compliance, which increases the therapeutic value of the drug. Designing and formulating a polypeptide drug delivery through the GI tract has been a persistent challenge because of their unfavorable physicochemical properties, which includes enzymatic degradation, poor membrane permeability and large molecular size. The main challenge is to improve the oral bioavailability from less than 1% to at least 30-50%. Various strategies currently under investigation include chemical modification, formulation vehicles and use of enzyme inhibitors, absorption enhancers and mucoadhesive polymers.

Clinical development of orally active peptide drugs has been restricted by their unfavorable physicochemical properties, which limit their intestinal mucosal permeation and their lack of stability against enzymatic degradation. Successful oral delivery of peptides will depend, therefore, on strategies designed to alter the physicochemical characteristics of these potential drugs, without changing their biological activity, in order to overcome the physical and biochemical barrier properties of the intestinal cells.

Digestive processes for proteins and peptides are catalyzed by a variety of enzymes that are specialized in the hydrolysis of peptide bonds. Due to the wide substrate specificity of these proteases and peptidases, it is not surprising that the metabolic activity in the intestinal lumen is a major barrier limiting the absorption of peptide-based drugs (Pauletti, "Improvement of oral peptide bioavailability: Peptidomimetics and prodrug strategies", *Advanced Drug Delivery Reviews,* 27: 235-256 (1997).

There is a need for selectively enhancing the pulmonary vasodilatory effect of compounds through co-administration with an orally active targeting peptide to increase the therapeutic efficacy through the unique formulation and administration.

SUMMARY OF THE INVENTION

Figure 1:
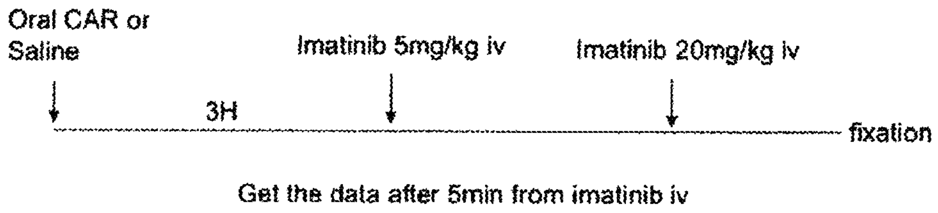
FIG. 1 shows the experimental design to determine the pulmonary selectivity of orally administered CAR prior to IV administration of two different doses of imatinib. Anesthetized severe occlusive PAH rats were then catheterized in the right jugular vein for measurement of right ventricular systolic pressure (RVSP), the right carotid artery and advanced into the aorta for the measurement of systemic pressure (SAP) and the left jugular vein for drug administration.

In one embodiment, the present invention provides for a composition comprising: (a) an orally active targeting peptide comprising a sequence substantially identical to CARSKNKDC (SEQ ID NO: 1), or a variant thereof, and (b) at least one therapeutic molecule which conveys a measurable therapeutic benefit to a disease selected from the group consisting of pulmonary hypertension, interstitial lung disease, acute lung injury (ALI), acute respiratory distress syndrome (ARDS), sepsis, septic shock, sarcoidosis of the lung, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs; inflammatory bowel disease, crohn's disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, inflammatory diseases, angiogenic diseases, wound healing, infections, trauma injuries and systemic connective tissue diseases including systemic lupus erythematosus, rheumatoid arthritis, scleroderma, polymyositis, dermatomyositis, and diabetes.

In another embodiment, the present invention additionally provides for a method of treating a pulmonary or fibrotic disease comprising: (a) providing an orally active targeting peptide comprising a sequence substantially identical to CARSKNKDC (SEQ ID NO: 1), or a variant thereof; (b) providing at least one therapeutic molecule which conveys a measureable therapeutic benefit to the disease; (c) co-administering a composition comprising (a) and (b) to an animal in need thereof; and (d) measuring a therapeutic benefit to the animal.

CAR may be administered in the linear form as depicted in SEQ ID NO: 1 or with a labeling agent, such as a fluorescent element (i.e. FAM-labeled CAR).

DETAILED DESCRIPTION OF THE INVENTION

Definitions

An "oral formulation" as referred to herein means formulating a peptide for oral administration in a manner including, but not limited to: pills, tablets, dissolving strips or tabs, chewing gum, dropper-prepared solutions, microspheres, liquids or gases.

The phrase "substantially identical" means that a relevant sequence is at least 70%, 75%, 80%, 85%, 90%, 92%, 95% 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions. Variants can comprise conservatively substituted sequences, meaning that a given amino acid residue is replaced by a residue having similar physiochemical characteristics. See Zubay, Biochemistry, Addison-Wesley Pub. Co., (1983). It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa.

In addition to the known functional variants, there are derivatives of the peptides disclosed herein which can also function in the disclosed methods and compositions. Protein and peptide variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein or peptide sequence. Typically, no more than about from 2 to 6 residues are deleted at any one site within the protein or peptide molecule. These variants can be prepared by site-specific mutagenesis of nucleotides in the DNA encoding the protein or peptide, thereby producing DNA encoding the variant, and thereafter expressing the DNA in recombinant cell culture, or via solid state peptide synthesis.

Techniques for making substitution mutations at predetermined sites in DNA having a known sequence are well known. Amino acid substitutions are typically of single residues, but can occur at a number of different locations at once; insertions usually will be on the order of about from 1 to 10 amino acid residues; and deletions will range about from 1 to 10 residues. Deletions or insertions preferably are made in adjacent pairs, i.e. a deletion of 2 residues or insertion of 2 residues. Substitutions, deletions, insertions or any combination thereof can be combined to arrive at a final construct. The mutations generally should not place the sequence out of reading frame (unless a truncated peptide is intended) and preferably will not create complementary regions that could produce secondary mRNA structure.

Substitutional variants are those in which at least one residue has been removed and a different residue inserted in its place. Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. Similarly, the term "conformational homology" may be used herein to define a sequence which maintains a similar arrangement of amino acids from a conformational perspective to SEQ ID NO:1 or SEQ ID NO:2.

As used herein, the term "peptide" is used broadly to mean peptides, proteins, fragments of proteins and the like. The peptide may be animal, bacterial, viral or synthetic in origin. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an .alpha.-methylated amino acid; .alpha., .alpha.-dialkylglycine or .alpha.-aminocycloalkane carboxylic acid; an N.sup..alpha.-C-.sup..alpha. cyclized amino acid; an N.sup..alpha..-methylated amino acid; a .beta.- or .gamma.-amino cycloalkane carboxylic acid; an .alpha., .beta.-unsaturated amino acid; a .beta., .beta.-dimethyl or .beta.-methyl amino acid; a .beta.-substituted-2,3-methano amino acid; an N—C.sup.epsilon or C.sup.alpha.-C.sup.delta. cyclized amino acid; a substituted proline or another amino acid mimetic. A peptidomimetic which mimics peptide secondary structure can contain, for example, a non-peptidic .beta.-turn mimic; .gamma.-turn mimic; mimic of .beta.-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

CARSKNKDC (SEQ ID NO: 1) (CAR) peptide has been previously been shown to target wound healing (Järvinen and Ruoslahti, 2007). CAR peptide has also been linked to decorin for targeted anti-TGF-β scar minimization in skin wounds (Järvinen and Ruoslahti, 2010).

Here we describe the novel homing of orally administered CAR peptides to hypertensive pulmonary vasculature, acutely injured pulmonary tissue, and fibrotic pulmonary tissue. Additionally, we disclose a novel means of achieving targeted therapy with orally administered CAR via simultaneous administration of CAR peptide along with another therapeutic.

As used herein, the term "therapeutic compound" shall mean a substance which is used in connection with an application that is therapeutic or diagnostic in nature, such as in methods for diagnosing the presence or absence of a disease in a patient and/or in methods for treating a disease in a patient. As to compatible therapeutic compounds, those skilled in the art will appreciate that any therapeutic or diagnostic agent may be incorporated in the stabilized dispersions of the present invention. For example, the therapeutic compound may be selected from the group consisting of antiallergics, bronchodilators, vasodilators, antihypertensive agents, bronchoconstrictors, pulmonary lung surfactants, analgesics, antibiotics, leukotriene inhibitors or antagonists, anticholinergics, mast cell inhibitors, antihistamines, anti-inflammatories, anti-neoplastics, anesthetics, anti-tuberculars, imaging agents, cardiovascular agents, enzymes, steroids, genetic material, viral vectors, antisense agents, small molecule drugs, proteins, peptides and combinations thereof. Particularly preferred therapeutic compounds comprise compounds which are to be administered systemically (i.e. to the systemic circulation of a patient) such as small molecule drugs, imaging agents, peptides, proteins or polynucleotides. As will be disclosed in more detail below, the bioactive agent may be incorporated, blended in, coated on or otherwise associated with the targeting peptide disclosed herein. Particularly preferred therapeutic compounds for use in accordance with the invention include anti-allergies, peptides and proteins, bronchodilators, anti-inflammatory agents and anti-cancer compounds for use in the treatment of disorders involving diseased tissue reflecting altered heparan sulfate variants specific to said disease. Yet another associated advantage of the present invention is the effective delivery of therapeutic compounds administered or combined with a targeting peptide.

Examples of therapeutic compounds include but are not limited to steroids, fibronectin, anticlotting drugs, anti-platelet function drugs, drugs which prevent smooth muscle cell growth on inner surface wall of vessel, heparin, heparin fragments, aspirin, coumadin, tissue plasminogen activator (TP A), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, integrins, insulin and GLP-1 agonists.

These findings provide the means to diagnose and deliver targeted therapies for diseases such as pulmonary hypertension, interstitial lung disease, acute lung injury (ALI), acute respiratory distress syndrome (ARDS), sepsis, septic shock, sarcoidosis of the lung, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs; inflammatory bowel disease, crohn's disease, ulcerative colitis, primary biliary cirrhosis, pancreatitis, interstitial cystitis, chronic obstructive pulmonary disease, atherosclerosis, ischemic heart disease, vasculitis, neoplastic/metastatic/ontological diseases (including cancer), pneumoconiosis, autoimmune diseases, inflammatory diseases, angiogenic diseases, wound healing, infections, trauma injuries and systemic connective tissue diseases including systemic lupus erythematosus, rheumatoid arthritis, scleroderma, polymyositis, dermatomyositis, and diabetes.

CARSKNKDC (SEQ ID NO: 1) (CAR) peptide has been previously shown to target wound healing (Järvinen and Ruoslahti, 2007). CAR peptide has also been linked to decorin for targeted anti-TGF-β scar minimization in skin wounds (Järvinen and Ruoslahti, 2010).

CAR peptide has previously been shown to home to pulmonary hypertensive arteries in monocrotaline (MCT) and SU5416/Hypoxia/Normoxia severe occlusive rat models of PAH. CAR peptide has also previously demonstrated acute pulmonary selective vasodilation when co-administered with the Rho-kinase inhibitor fasudil. Recently we sought to explore the hemodynamic effect of orally administering 20 mg/kg of CAR 3 hours prior to i.v. administration of imatinib at doses of 5 mg/kg and 20 mg/kg in a severe occlusive rat model of PAH. Rats were first orally syringe fed a mixture of 20 mg/Kg CAR in a 10% sucrose solution 3 hours prior to anesthetization and assessment of the hemodynamic effects of i.v. administration of 5 mg/kg imatinib followed 20 minutes later by i.v. administration of 20 mg/kg of imatinib (FIG. 1).

Figure 2:
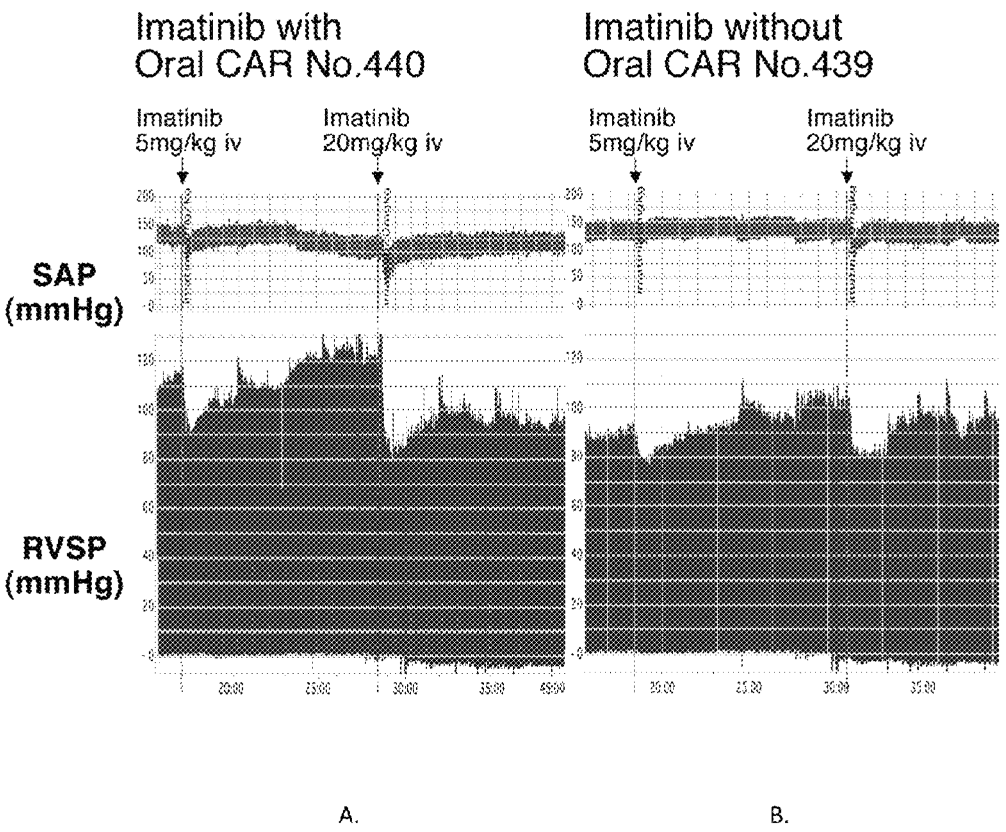
FIG. 2 shows the selective adjuvant activity of CAR peptide displayed 3 hours after oral administration.
Figure 3:
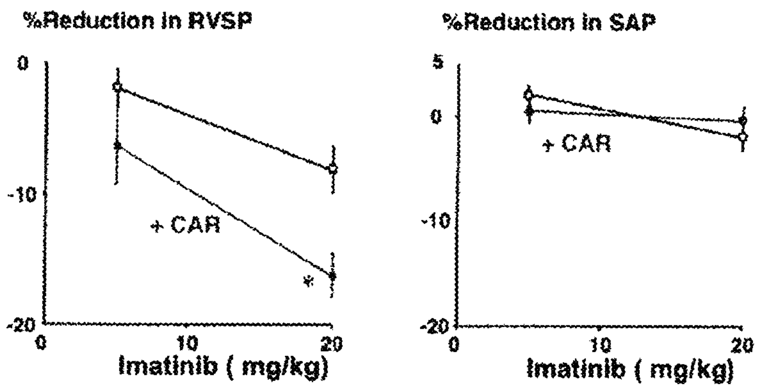
FIG. 3 shows dose-response curves for imatinib (iv, bolus) with (blue line) or without oral CAR (20 mg/kg) for right ventricular systolic pressure (RVSP) and systemic arterial pressure (SAP) in SU5416/Hx/Nx-exposed 5 wk PAH rats. Values are means±SE. N=3 without CAR and N=5 with CAR *p<0.05 vs. without CAR.
Figure 4:
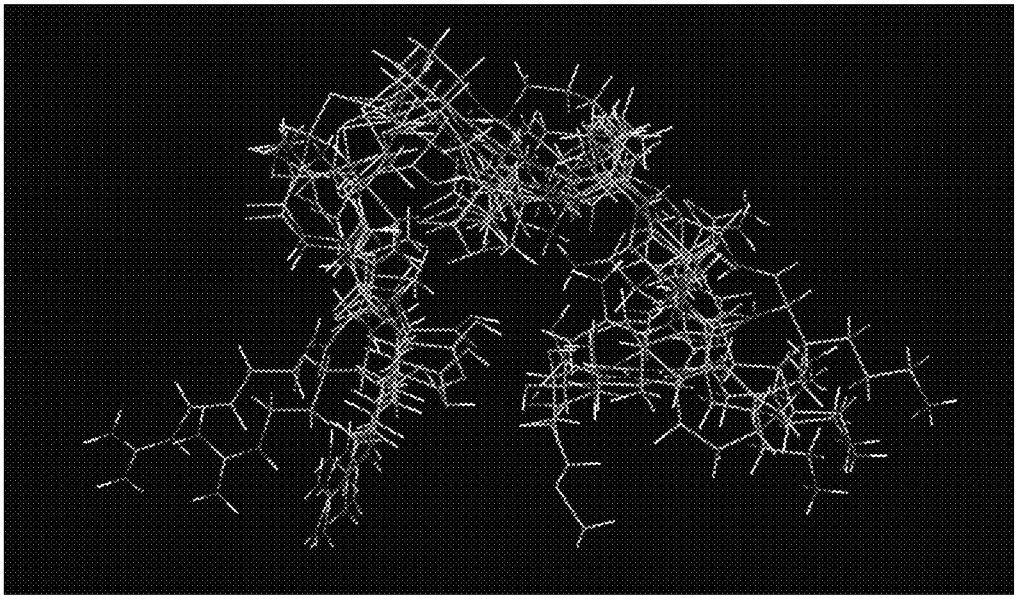
FIG. 4 shows a superposition image of CAR variants with single amino acid substitutions shown in FIGS. 5-10.

CAR peptide displayed pulmonary selective adjuvant activity 3 hours after oral administration (FIG. 2). When imatinib was administered 3 hours after oral CAR administration at a dose of 20 mg/kg, it resulted in an acute selective pulmonary hypotensive reduction in right ventricular systolic pressure (RVSP) of 18% with no change in systemic arterial pressure (SAP) (FIG. 3).

The present invention provides a new paradigm in the treatment of pulmonary hypertension, using an orally active, cell-penetrating homing peptide that, when combined with existing PAH therapies, enables the selective treatment of this disease.

These diseases can be treated by simultaneously administering CAR peptide with the bioactive agent to be targeted to the site of disease. We define simultaneous administration, or co-administration, as administration of CAR followed by administration of the therapeutic to be targeted within 1 hour of CAR administration. For example, if the disease is pulmonary hypertension and the desired goal is targeted pulmonary arterial vasodilation, an effective dose of CAR peptide can be co-administered with a minimal dose of systemic vasodilator to achieve targeted pulmonary vasodilation and a significant decrease in pulmonary pressure with minimal systemic hypotension.

Similarly, CAR peptide can be co-administered with other medications to increase therapeutic bioavailability, boost therapeutic efficacy, and minimize side effects. CAR may be administered in a linear or cyclical form, or in any conformation deemed physiologically appropriate as a means of conveying treatment.

In addition to targeted vasodilation, we can also deliver targeted anti-coagulation. For example, in a disease like acute lung injury, which is often marked by pulmonary intra-alveolar coagulation, targeted anti-coagulation can be delivered to the affected pulmonary area by co-administering an effective dose of CAR with an anti-coagulant such as tissue factor pathway inhibitor (TFPI) or site-inactivated factor Vila (Welty-Wolf et al., 2001) in a minimal dose to achieve targeted pulmonary anticoagulation with minimal changes in clotting ability over the areas of the body not undergoing thrombosis. Selective pulmonary anti-coagulation can also be utilized to treat other pulmonary diseases marked by pulmonary thrombosis such as pulmonary hypertension, lung transplant rejection and others.

In a disease like chronic obstructive pulmonary disease, which is often marked by shortness of breath, CAR peptide can be co-administered to boost the effective concentration and potency of drugs to relax airway smooth muscles such as long lasting β-2 agonists such as salmeterol or formoterol (Richter, et al., 2002).

Many pulmonary diseases are often marked by a decrease in glutathione (GSH), a powerful antioxidant (Morris and Bernard, 1994). CAR peptide can be co-administered with N-Acetylcysteine (NAC), a glutathione precursor, in diseases like pulmonary fibrosis, PAH, ALI, and other pulmonary disorders to boost GSH production and scavenge reactive oxidants often found in pulmonary diseases. GSH may also serve to dampen the inflammatory immune response by binding to triggering receptor expressed on myeloid cells 1 (TREM 1) and diminishing monocyte/macrophage- and neutrophil-mediated inflammatory responses. Co-administration of CAR with NAC can serve to lessen the severe inflammatory immune response that often characterizes severe pulmonary and fibrotic diseases like ALI, pulmonary hypertension, autoimmune diseases and many other conditions.

The levels of antioxidants such as Superoxide Dismutase (SOD) (Rosenfeld, et al., 1996), or synthetic superoxide dismutase mimetics like EUK-8 (Gonzalez et al., 1996) can be increased through co-administration of CAR.

Treatments for pulmonary diseases like pulmonary fibrosis, PAH and ALI can also be improved by co-administering CAR with TGF-β inhibitors like decorin. Decorin, which has been previously enhanced through direct conjugation with CAR (Järvinen and Ruoslahti, 2010), can also be co-administered with CAR to achieve the benefits of targeting without direct conjugation between the CAR and decorin molecules.

In pulmonary hypertension, pulmonary fibrosis and other pulmonary diseases, the benefits of endothelin (ET-1) receptor antagonists (Kuklin et al., 2004), prostacyclin derivatives (Olschewski et al., 1999), phosphodiesterase type 5 inhibitors (Kanthapillai et al,. 2004) and oncological agents such as imatinib (Ghofrani et al., 2005) (Aono et al., 2005) can be increased for patients through the co-administration of CAR.

Other pulmonary and fibrotic disease treatments such as Ketoconazole which inhibits thromboxane and leukotriene synthesis (Sinuff e al., 1999) can be improved in its efficacy while minimizing side effects through co-administration with CAR.

Newer therapeutic approaches such as small interfering RNA (siRNA), and microRNA (miRNA) therapies (Wurdinger and Costa, 2007) can also be improved and side effects minimized through the selective targeting of diseased tissue through the co-administration of CAR.

In addition to targeted therapies, CAR's homing to diseased pulmonary and fibrotic tissues can be utilized for the purposes of diagnosis through the conjugation or co-administration of CAR with imaging agents.

EXAMPLES

I. Linear Peptide Variants

The molecular and electrostatic potential structure of the sequences described herein can be modeled, and compared to substitutional variants in which one or more amino acids have been substituted to predict if the variant will have a similar conformation with an expected similar function. The linear peptide variants are shown in FIGS. 4-10.

The conformation of peptide variants can be modeled using molecular and electronic structure modeling programs like MOLDEN.

Figure 5:
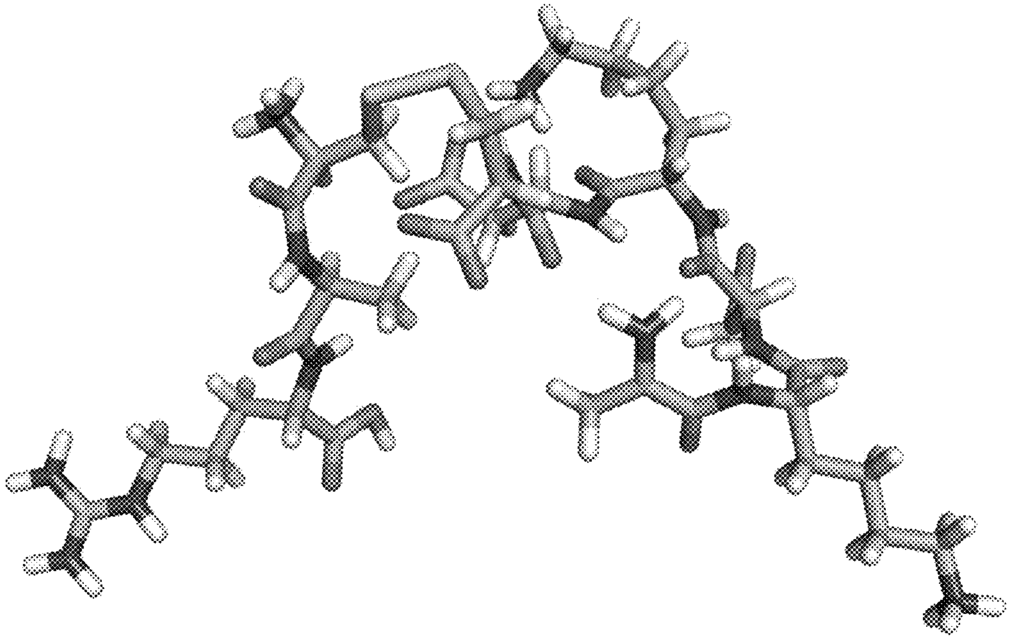
FIG. 5 shows a molecular structural model of CAR variant AKNKDCCAR (SEQ ID NO: 2) in which alanine (A) has been substituted for the N terminus cysteine (C).
Figure 6:
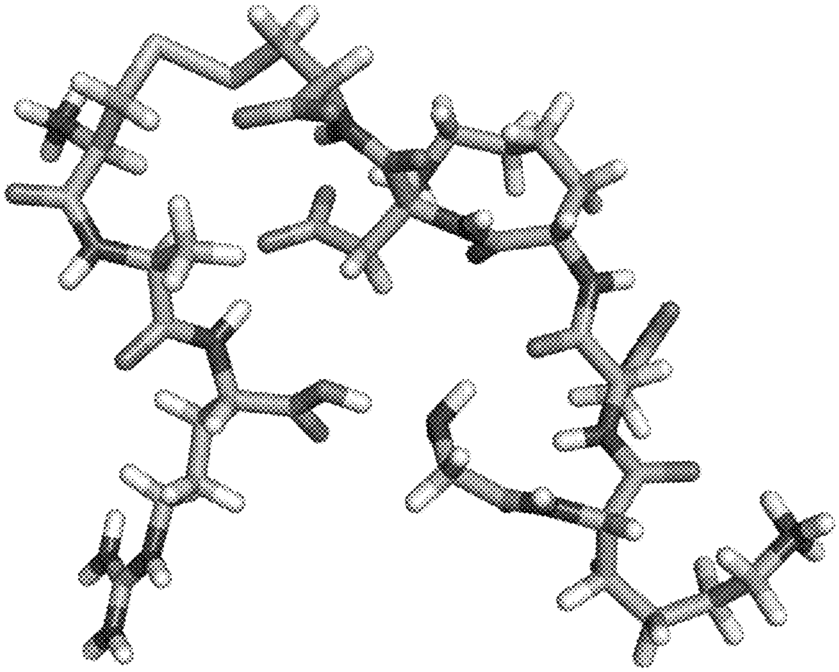
FIG. 6 shows a molecular structural model of CAR variant GKNKDCCAR (SEQ ID NO: 3) in which glutamic acid (G) has been substituted for the N terminus cysteine (C).
Figure 7:
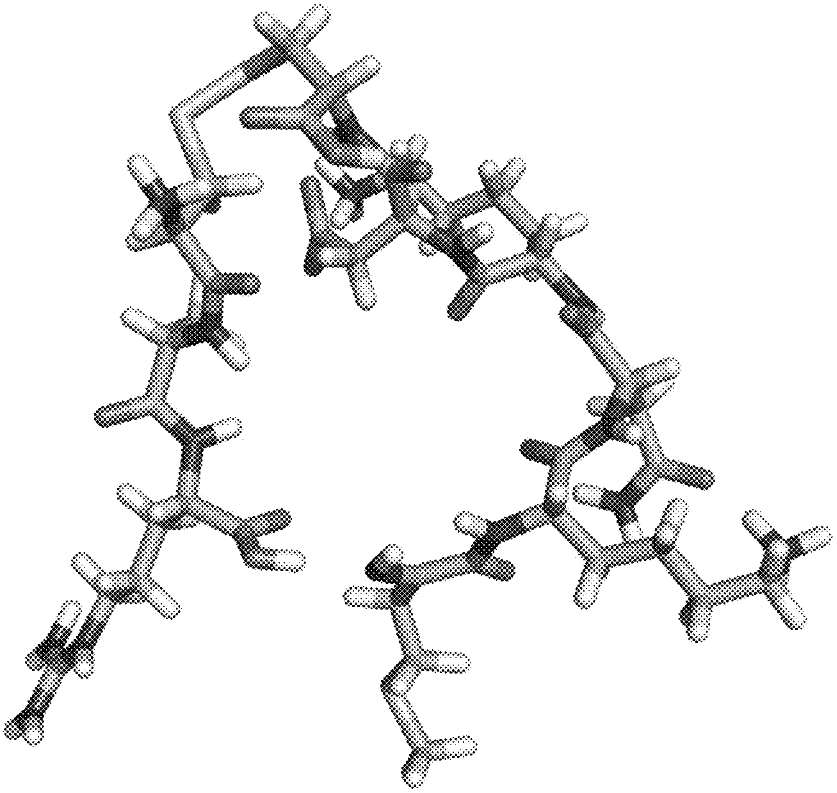
FIG. 7 shows a molecular structural model of CAR variant MKNKDCCAR (SEQ ID NO: 4) in which methionine (M) has been substituted for the N terminus cysteine (C).
Figure 8:
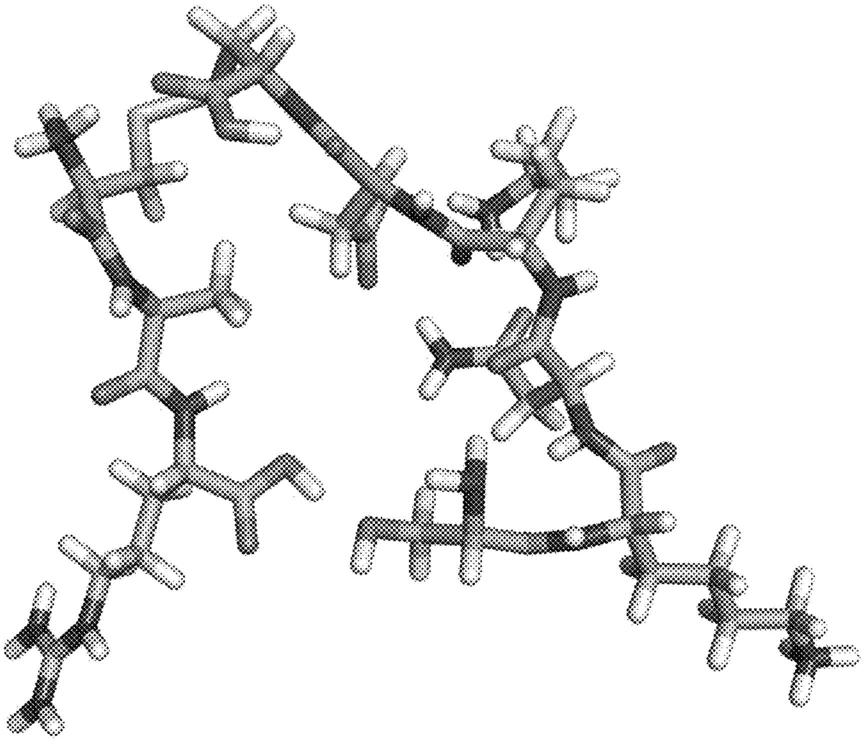
FIG. 8 shows a molecular structural model of CAR variant SKNKDCCAR (SEQ ID NO: 5) in which serine (S) has been substituted for the N terminus cysteine (C).
Figure 9:
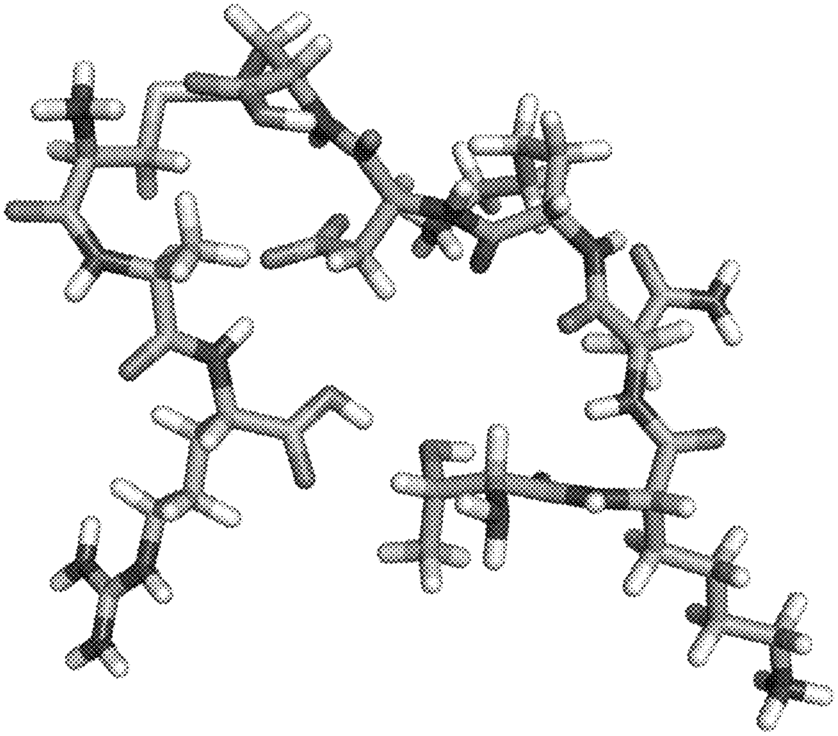
FIG. 9 shows a molecular structural model of CAR variant TKNKDCCAR (SEQ ID NO: 6) in which in which Threonine (T) has been substituted for the N terminus cysteine (C).
Figure 10:
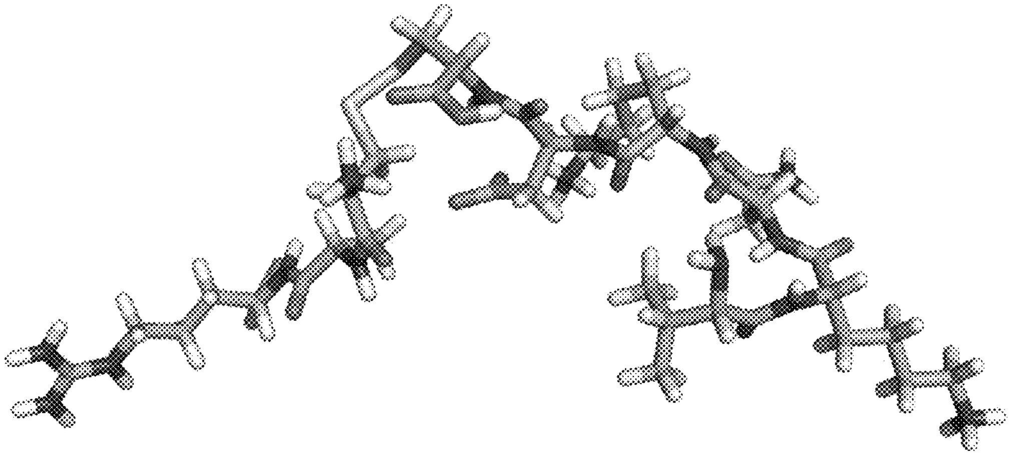
FIG. 10 shows a molecular structural model of CAR variants VKNKDCCAR (SEQ ID NO: 7) in which Valine (V) has been substituted for the N terminus cysteine (C).
Figure 11:
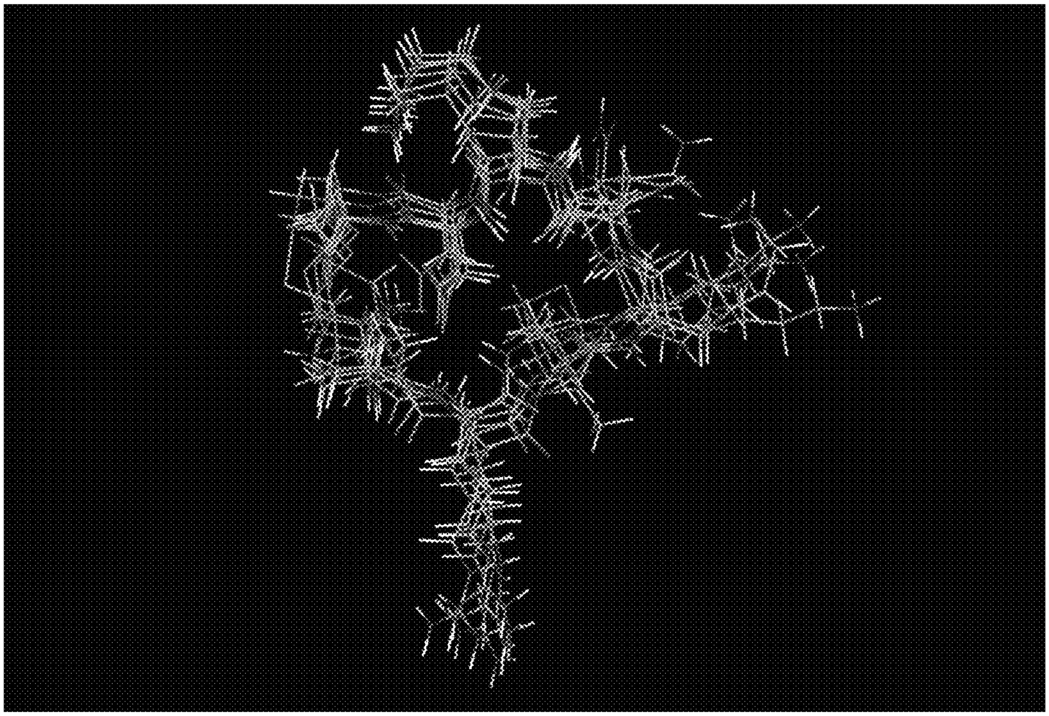
FIG. 11 shows a superposition image of cyclic CAR variants with single amino acid substitutions shown in FIGS. 12-17.

The sequences from the library of single amino acid substitutional variants were as follows:

```
                    (SEQ ID NO: 2; FIG. 5)
AKNKDCCAR

                    (SEQ ID NO: 3; FIG. 6)
GKNKDCCAR

                    (SEQ ID NO: 4; FIG. 7)
MKNKDCCAR

                    (SEQ ID NO: 5; FIG. 8)
SKNKDCCAR

                    (SEQ ID NO: 6; FIG. 9)
TKNKDCCAR

                   (SEQ ID NO: 7; FIG. 10)
VKNKDCCAR
```

II. Cyclic Peptide Variants

The sequences were modeled in an energy minimized state and an electrostatic potential map was created to visualize its electrostatic surface (FIGS. 11-17). A library of single amino acid substitutional variants of SEQ ID NO:1 were created.

Figure 12:
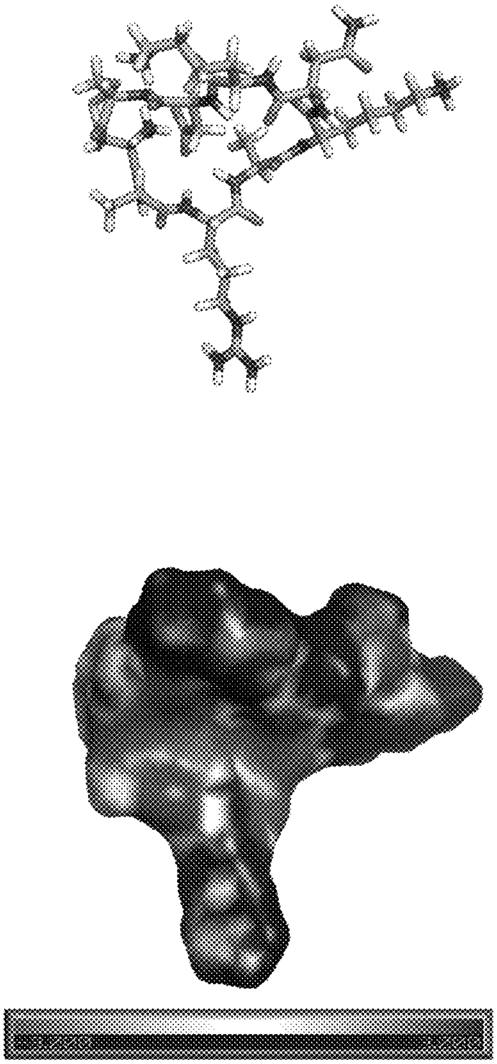
FIG. 12 shows a molecular structural model (top image) and electrostatic potential surface structure (bottom image) of cyclic CAR variant CARAKNKDC (SEQ ID NO: 8) in which alanine (A) has been substituted for the serine (S).
Figure 13:
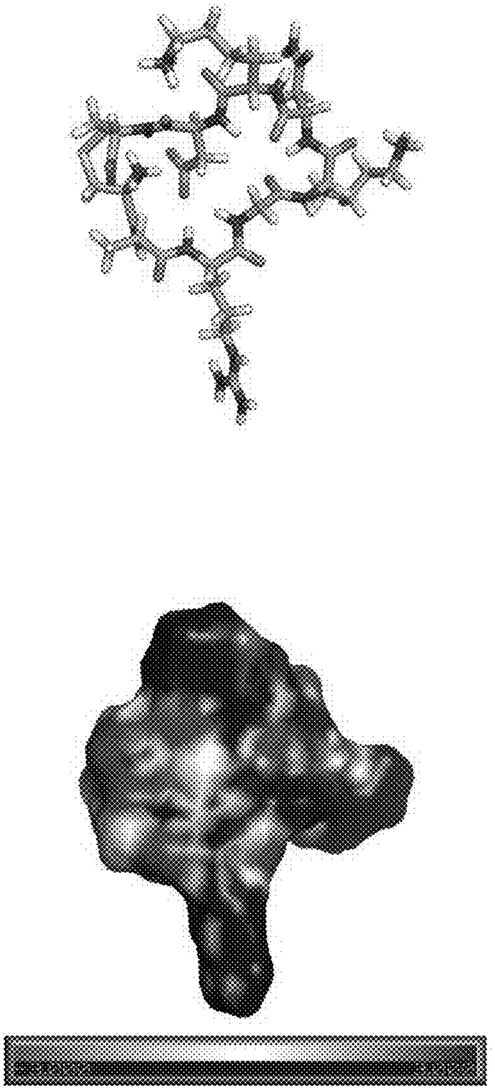
FIG. 13 shows a molecular structural model (top image) and electrostatic potential surface structure (bottom image) of cyclic CAR variant CARGKNKDC (SEQ ID NO: 9) in which glutamic acid (G) has been substituted for the serine (S).
Figure 14:
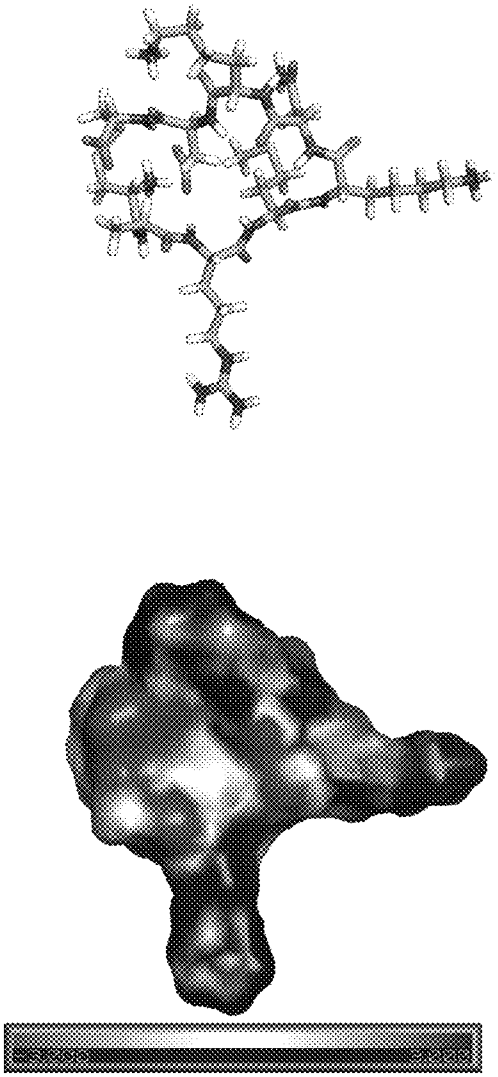
FIG. 14 shows a molecular structural model (top image) and electrostatic potential surface structure (bottom image) of cyclic CAR variant CARMKNKDC (SEQ ID NO: 10) in which methionine (M) has been substituted for the serine (S).
Figure 15:
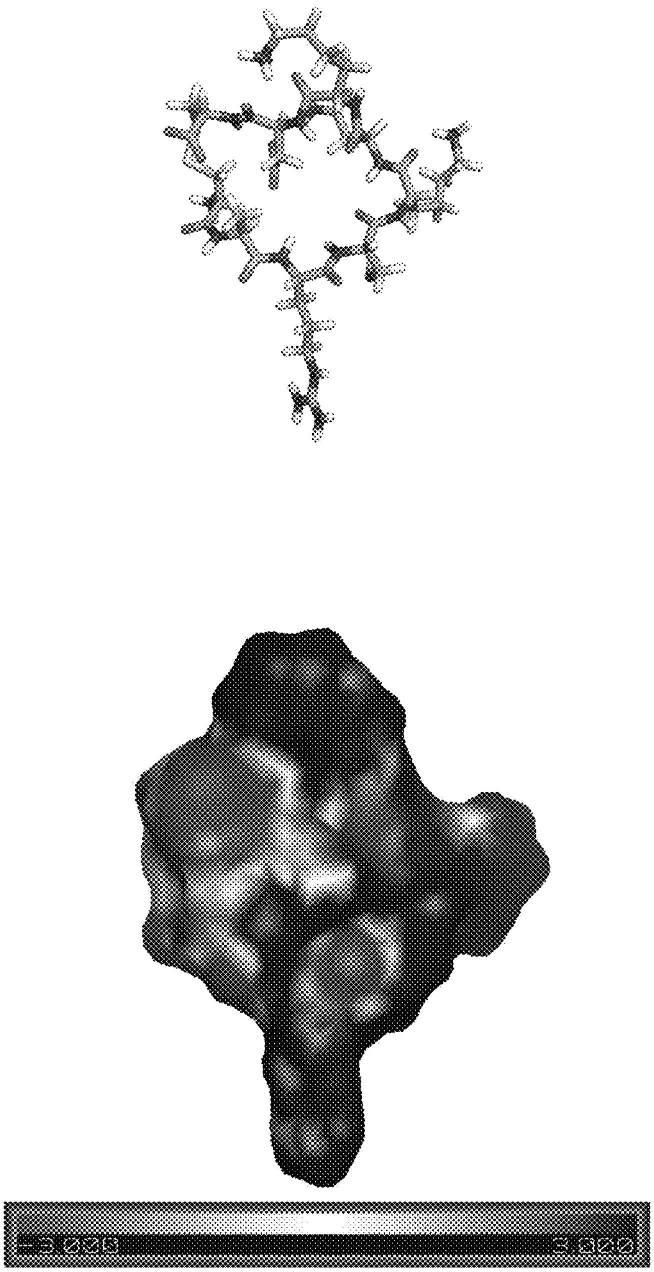
FIG. 15 shows a molecular structural model (top image) and electrostatic potential surface structure (bottom image) of cyclic CAR CARSKNKDC (SEQ ID NO: 1).

The sequences from the library of single amino acid substitutional variants were as follows:

```
                   (SEQ ID NO: 8; FIG. 12)
CARAKNKDC

                   (SEQ ID NO: 9; FIG. 13)
CARGKNKDC

                  (SEQ ID NO: 10; FIG. 14)
CARMKNKDC

                   (SEQ ID NO: 1; FIG. 15)
CARAKNKDC
```

-continued

Figure 16:
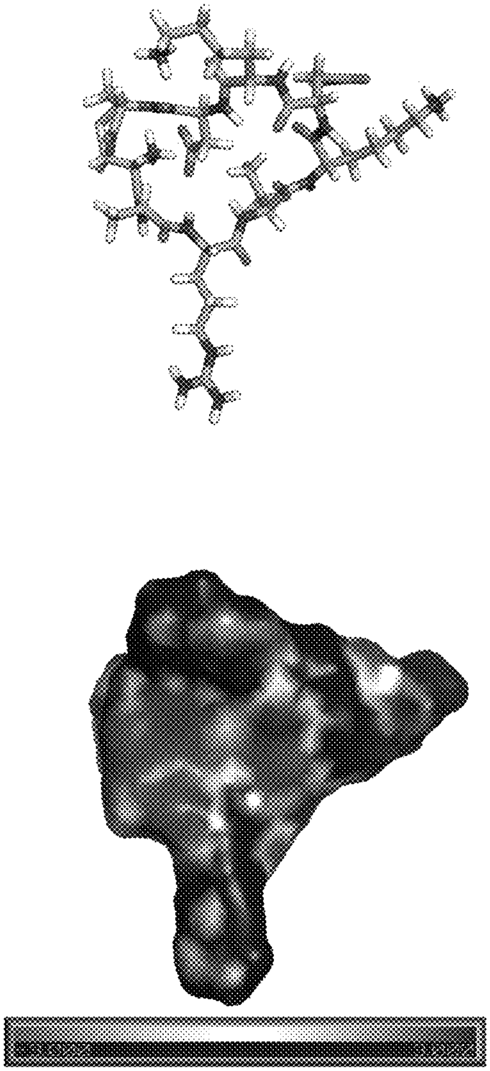
FIG. 16 shows a molecular structural model (top image) and electrostatic potential surface structure (bottom image) of cyclic CAR variant CARTKNKDC (SEQ ID NO: 11) in which Threonine (T) has been substituted for the serine (S).
Figure 17:
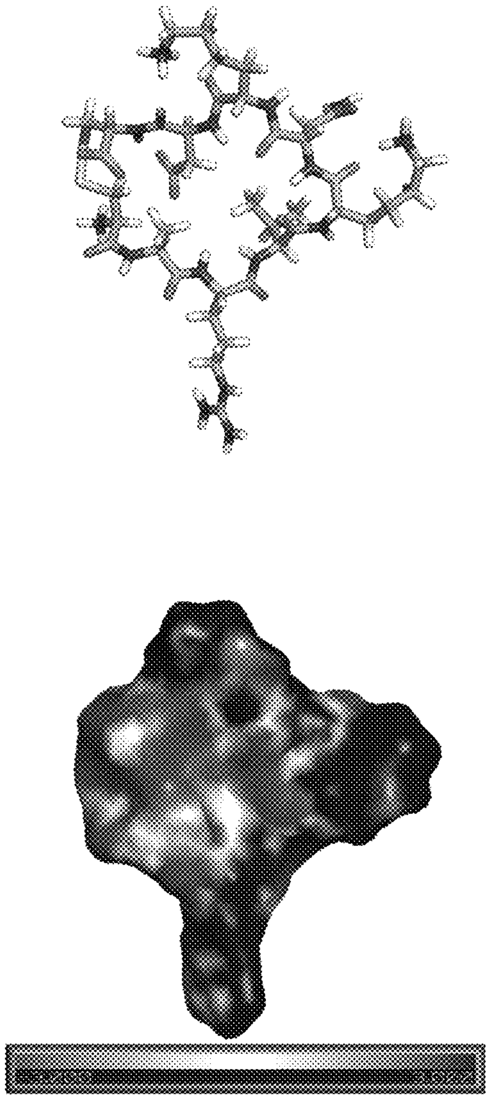
FIG. 17 shows a molecular structural model (top image) and electrostatic potential surface structure (bottom image) of cyclic CAR variant CARVKNKDC (SEQ ID NO: 12) in which Valine (V) has been substituted for the serine (S).

```
                  (SEQ ID NO: 11; FIG. 16)
CARTKNKDC

                  (SEQ ID NO: 12; FIG. 17)
CARVKNKDC
```

III. CAR Administration

Figure 18:
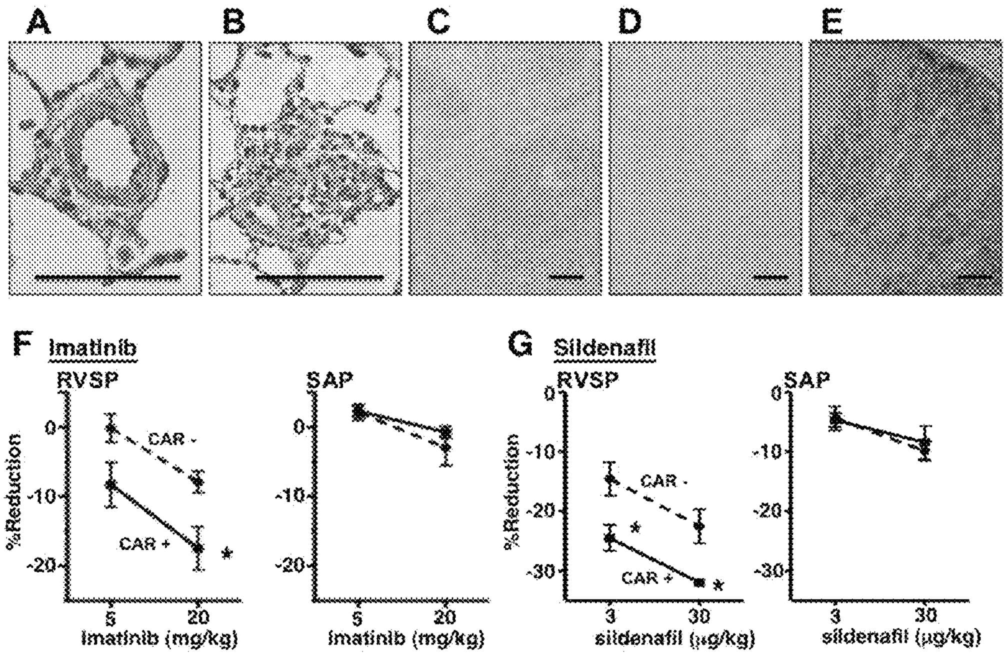
FIG. 18 shows the distribution of sublingually administered CAR. (A) a pulmonary artery with medial thickening, (B) a small pulmonary artery with neointimal occlusion, (C) spleen, (D) liver, and (E) kidney from a SU/Hx/Nx rat. Scale bar shows 100 mm. Effects of CAR (3 mg/kg, sublingual) on intravenous (bolus) imatinib (F)- and sildenafil (G)-induced reductions in right ventricular systolic pressure (RVSP) and systemic arterial pressure (SAP) in SU/Hx/Nx rats. Values are means±SE. N=4-6. *$p<0.05$ with (solid line) vs. without (dashed line) CAR.

CAR was administered sublingually at a dosing of 3 mg/kg. The administration was performed in six rats with severe occlusive model PAH via dropper sublingually. The administration was +/− imatinib or +/− sildenafil. Results are shown in FIG. 18.

The data demonstrates that when taken orally, CAR can facilitate the selective action of co-administered drugs at the site of the disease, in the present case localized pulmonary vasodilation in PAH. When combined with the known qualities of CAR, i.e. homing and internalization of a wide range of diseased tissue, such as wounds, tumors, fibrosis, inflammation, and hypertensive tissue, and facilitation of selective update of a wide variety of co-administered compounds to enhance wound healing, the present invention provides an orally active CAR peptide that is able to facilitate the action of co-administered drugs in a selective manner to the sites of various diseases to which CAR has previously demonstrated homing activity. In a preferred embodiment, since CAR is known to home to wounds, orally active CAR may be combined with co-administered antibiotics or anti-scarring agents. In another preferred embodiment, since CAR is known to home to tumors and angiogenic tissues, orally active CAR may be combined with chemotherapeutic agents. In still another preferred embodiment, orally active CAR may be combined with antifibrotic agents for selective delivery to fibrotic tissue. In still another preferred embodiment, orally active CAR may be combined with anti-inflammatory agents for selective delivery to sites of inflammation. In still another preferred embodiment, orally active CAR may be combined with anti-asthmatic agents for selective delivery to the sites of asthma.

IV. Cyclic CARSKNKDC (CAR) Peptide Trypsin Digest Time-Course Experiment

In an effort to further understand the oral availability of cyclic CAR peptide, we tested the stability of cyclic CAR (cCAR) and linear CAR in the presence of trypsin, a serine protease that is one of the primary enzymes found in the digestive system of vertebrates. Trypsin selectively cleaves peptide chains at the carboxyl side of the basic residues lysine and arginine, yielding a potentially wide variety of peptide fragments.

We conducted a trypsin proteolysis time course experiment, and tested cCAR and linear CAR (cyclic CAR that lacks the disulfide bond between adjacent cysteine residues and has a linear structure) in the presence of a trypsin solution.

For the digest time course experiment, the cCAR peptide sample was prepared by dissolving cCAR in Krebbs buffer (670 μM CAR), and the trypsin digest solution was prepared by adding trypsin to Krebbs buffer as well (0.1 μg/μL, Trypsin). 15 μL CAR (670 μM) was added to 40 μL, trypsin solution (0.1 μg/μL) and 75 μL Krebbs buffer. The reaction was allowed to proceed at 24° C. for different time periods of time. The reactions were quenched with 20 μL formic acid (500 μM) at different time points to stop trypsin from degrading any further peptide substrate. These steps were performed repeatedly for multiple time points (t=0, 5, 10, 15, 20, 30, 60, 120 minutes) for both cCAR and linear CAR. The different time point samples were desalted and analyzed using mass spectrometry.

The subsequent mass spectrometry analysis of the enzymatic metabolites showed that the cCAR-trypsin digest yielded one predominant product that persisted over the time course of the experiment. When further analyzed, we found the product to be the cCAR peptide singly cleaved into the sequence SKNKDCCAR (SEQ ID NO: 5). This fragment is very similar to cCAR (disulfide intact and same amino acid residues present) but has been linearized at the arginine residue from the proteolytic actions of trypsin. An unexpected result of the experiment was that the fragment proved to be largely resistant to further degradation by trypsin.

In contrast, linear CAR was quickly digested by trypsin into its constituent amino acids at early time points in the trypsin digest experiment, with no singly cleaved products persisting.

SEQ ID NO: 5 was determined to be approximately 10 fold more resistant to trypsin digestion than cCAR, and approximately 100 fold more resistant than linear CAR.

The predominance of the SKNKDCCAR product in the trypsin digest experiment as well as its unexpected resistance to further degradation by trypsin may help explain the oral availability of cCAR. Furthermore, SKNKDCCAR may itself have intrinsic, unique, therapeutic properties and oral availability to cCAR.

What is claimed is:

1. A composition comprising:

a) an orally active targeting peptide comprising a sequence, the sequence consisting of at least one member selected from the group consisting of SEQ ID NO: 2, SEQ ID NO: 3, SEQ ID NO: 4, SEQ ID NO: 5, SEQ ID NO: 6 and SEQ ID NO: 7, SEQ ID NO: 8, SEQ ID NO: 9, SEQ ID NO: 10, SEQ ID NO: 11, and SEQ ID NO: 12; and (b) at least one therapeutic compound which conveys a measureable therapeutic benefit to an individual suffering from a disease.

2. The composition of claim 1, wherein the targeting peptide is animal, bacterial, viral or synthetic in origin.

3. The composition of claim 1, wherein the disease is selected from the group consisting of pulmonary hypertension, interstitial lung disease, acute lung injury (ALI), acute respiratory distress syndrome (ARDS), sepsis, septic shock, sarcoidosis of the lung, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, nonalcoholic steatohepatitis, sarcoidosis of the lymph nodes, or other organs; inflammatory bowel disease, Crohn's disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, inflammatory diseases, angiogenic diseases, wound healing, infections, trauma injuries and systemic connective tissue diseases including systemic lupus erythematosus, rheumatoid arthritis, scleroderma, polymyositis, dermatomyositis, and diabetes.

4. The composition of claim 3, wherein the disease is pulmonary hypertension.

5. The composition of claim 1, wherein the at least one therapeutic compound is specific for the disease from which the individual is suffering.

* * * * *

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: Synthesized

<400> SEQUENCE: 1

Cys Ala Arg Ser Lys Asn Lys Asp Cys
1               5


<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Ala Lys Asn Lys Asp Cys Cys Ala Arg
1               5


<210> SEQ ID NO 3
<211> LENGTH: 9
<212> TYPE: PRT
<213> ORGANISM: Artificial Sequence
<220> FEATURE:
<223> OTHER INFORMATION: Synthesized

<400> SEQUENCE: 3

Gly Lys Asn Lys Asp Cys Cys Ala Arg
1               5


<210> SEQ ID NO 4
<211> LENGTH: 9
<212> TYPE: PRT
<213> ORGANISM: Artificial Sequence
<220> FEATURE:
<223> OTHER INFORMATION: Synthesized

<400> SEQUENCE: 4

Met Lys Asn Lys Asp Cys Cys Ala Arg
1               5


<210> SEQ ID NO 5
<211> LENGTH: 9
<212> TYPE: PRT
<213> ORGANISM: Artificial Sequence
<220> FEATURE:
<223> OTHER INFORMATION: Synthesized
```

<400> SEQUENCE: 5

Ser Lys Asn Lys Asp Cys Cys Ala Arg
1 5

<210> SEQ ID NO 6
<211> LENGTH: 9
<212> TYPE: PRT
<213> ORGANISM: Artificial Sequence
<220> FEATURE:
<223> OTHER INFORMATION: Synthesized

<400> SEQUENCE: 6

Thr Lys Asn Lys Asp Cys Cys Ala Arg
1 5

<210> SEQ ID NO 7
<211> LENGTH: 9
<212> TYPE: PRT
<213> ORGANISM: Artificial Sequence
<220> FEATURE:
<223> OTHER INFORMATION: Synthesized

<400> SEQUENCE: 7

Val Lys Asn Lys Asp Cys Cys Ala Arg
1 5

<210> SEQ ID NO 8
<211> LENGTH: 9
<212> TYPE: PRT
<213> ORGANISM: Artificial Sequence
<220> FEATURE:
<223> OTHER INFORMATION: Synthesized

<400> SEQUENCE: 8

Cys Ala Arg Ala Lys Asn Lys Asp Cys
1 5

<210> SEQ ID NO 9
<211> LENGTH: 9
<212> TYPE: PRT
<213> ORGANISM: Artificial Sequence
<220> FEATURE:
<223> OTHER INFORMATION: Synthesized

<400> SEQUENCE: 9

Cys Ala Arg Gly Lys Asn Lys Asp Cys
1 5

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

Cys Ala Arg Met Lys Asn Lys Asp Cys
1 5

<210> SEQ ID NO 11
<211> LENGTH: 9
<212> TYPE: PRT
<213> ORGANISM: Artificial Sequence
<220> FEATURE:
<223> OTHER INFORMATION: Synthesized -continued

```
<400> SEQUENCE: 11

Cys Ala Arg Thr Lys Asn Lys Asp Cys
1               5


<210> SEQ ID NO 12
<211> LENGTH: 9
<212> TYPE: PRT
<213> ORGANISM: Artificial Sequence
<220> FEATURE:
<223> OTHER INFORMATION: Synthesized

<400> SEQUENCE: 12

Cys Ala Arg Val Lys Asn Lys Asp Cys
1               5
```

UNITED STATES PATENT AND TRADEMARK OFFICE
CERTIFICATE OF CORRECTION

PATENT NO. : 9,655,973 B2
APPLICATION NO. : 14/383818
DATED : May 23, 2017
INVENTOR(S) : Mann Page 1 of 2

It is certified that error appears in the above-identified patent and that said Letters Patent is hereby corrected as shown below:

In the Specification

Column 1, Line 58: replace the word "on" with the word "of";

Column 1, Line 61: the word "element" should read "elements";

Column 3, Line 54: replace the ";" with a ":";

Column 4, Line 41: replace the word "have" with the word "has";

Column 4, Line 43: insert a --,-- after the word "peptide";

Column 4, Line 43: insert a --,-- after the word "agent";

Column 4, Line 43: delete the word "which";

Column 5, Line 13: delete the phrase "useful for";

Column 5, Line 44: replace the word "their" with the word "the";

Column 5, Line 45: the word "includes" should read "include";

Column 8, Line 40: replace the ";" with a ":";

Column 8, Line 47: delete the second occurrence of the word "in";

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

Column 12, Line 33: replace the phrase "such as" with the word "like"; and

Column 14, Line 21: replace the word "update" with the word "uptake".